US010285786B2

(12) United States Patent
Fisker

(10) Patent No.: US 10,285,786 B2
(45) Date of Patent: May 14, 2019

(54) CUSTOMIZED DENTAL ABUTMENT FORMED OF TWO CUSTOMIZED PARTS

(71) Applicant: 3Shape A/S, Copenhagen K (DK)

(72) Inventor: Rune Fisker, Virum (DK)

(73) Assignee: 3Shape A/S, Copenhagen K (DK)

( * ) Notice: Subject to any disclaimer, the term of this patent is extended or adjusted under 35 U.S.C. 154(b) by 750 days.

(21) Appl. No.: 14/362,938

(22) PCT Filed: Dec. 6, 2012

(86) PCT No.: PCT/EP2012/074621
§ 371 (c)(1),
(2) Date: Jun. 5, 2014

(87) PCT Pub. No.: WO2013/083683
PCT Pub. Date: Jun. 13, 2013

(65) Prior Publication Data
US 2014/0315152 A1 Oct. 23, 2014

Related U.S. Application Data

(60) Provisional application No. 61/568,321, filed on Dec. 8, 2011.

(30) Foreign Application Priority Data

Dec. 7, 2011 (DK) .................................. 2011 00951

(51) Int. Cl.
A61C 8/00 (2006.01)
A61C 13/00 (2006.01)
G16H 20/40 (2018.01)
(52) U.S. Cl.
CPC ............ A61C 8/0063 (2013.01); A61C 8/005 (2013.01); A61C 8/0012 (2013.01);
(Continued)

(58) Field of Classification Search
CPC .......................................... A61C 8/00–8/0098
(Continued)

(56) References Cited

U.S. PATENT DOCUMENTS 5,030,095 A 7/1991 Niznick
5,116,225 A * 5/1992 Riera ..................... A61C 8/005
433/173
(Continued)

FOREIGN PATENT DOCUMENTS

EP 2 324 795 A1 5/2011
EP 2 343 025 A2 7/2011
(Continued)

OTHER PUBLICATIONS

International Search Report (PCT/ISA/210) dated Feb. 15, 2013, by the European Patent Office as the International Searching Authority for International Application No. PCT/EP2012/074621.
(Continued)

Primary Examiner — Yogesh P Patel
(74) Attorney, Agent, or Firm — Buchanan Ingersoll & Rooney P.C.

(57) ABSTRACT

Disclosed is a dental prosthesis including an implant, a customized abutment, a restoration and an implant screw for securing the customized abutment to the implant, wherein the implant includes a screw bore extending from a first end of the implant for receiving at last a part of the implant screw, the customized abutment includes a through-going bore for receiving at least a part of the implant screw, the screw bore and the through-going bore are coaxially aligned along an implant axis when the implant screw is arranged in the screw and through-going bore, the abutment includes a customized abutment base and a customized abutment top where the customized abutment base and the customized abutment top defines an assembly axis along which they (Continued)

were assembled during manufacturing, where the implant axis is different from the assembly axis.

12 Claims, 4 Drawing Sheets

(52) U.S. Cl.
CPC ........ *A61C 8/0068* (2013.01); *A61C 13/0004* (2013.01); *A61C 8/0053* (2013.01); *F04C 2270/041* (2013.01); *G16H 20/40* (2018.01)

(58) Field of Classification Search
USPC ...................................... 433/172–176, 201.1
See application file for complete search history.

(56) References Cited

U.S. PATENT DOCUMENTS

| | | | |
|---|---|---|---|
| 5,281,140 A | 1/1994 | Niznick | |
| 5,527,182 A | 6/1996 | Willoughby | |
| 5,577,912 A | 11/1996 | Prins | |
| 6,250,922 B1 | 6/2001 | Bassett et al. | |
| 2002/0127518 A1* | 9/2002 | Lustig | A61C 8/0001 433/173 |
| 2003/0031982 A1 | 2/2003 | Abarno | |
| 2005/0266381 A1* | 12/2005 | Abarno | A61C 1/084 433/173 |
| 2008/0163067 A1 | 6/2008 | Berckmans et al. | |
| 2009/0047629 A1* | 2/2009 | Kim | A61C 8/005 433/173 |
| 2010/0304334 A1 | 12/2010 | Layton | |
| 2011/0097687 A1 | 4/2011 | Engman | |
| 2011/0123948 A1* | 5/2011 | Hinrichsen | A61C 8/005 433/173 |
| 2011/0224955 A1 | 9/2011 | Fisker et al. | |

FOREIGN PATENT DOCUMENTS

| | | |
|---|---|---|
| KR | 2010-0090564 A | 8/2010 |
| WO | WO 2010/088754 A1 | 8/2010 |

OTHER PUBLICATIONS

Office Action dated Nov. 24, 2017 in corresponding European Patent Application No. 12 798 709.7.

* cited by examiner

CUSTOMIZED DENTAL ABUTMENT FORMED OF TWO CUSTOMIZED PARTS

FIELD OF THE INVENTION

The invention relates to a customisable dental abutment for use with a dental implant and a restoration to form a dental prosthesis. In particular the invention relates to a dental prosthesis comprising a two-piece abutment wherein both pieces are customisable. This provides for an abutment which is both durable and allows for a more esthetical restoration than previously known.

The invention furthermore relates to a method for designing the two-piece abutment and to a method for producing said abutment.

BACKGROUND OF THE INVENTION

Within restorative dentistry high customisability is often desired. This is due to the highly varied anatomy of the set of teeth for each human, which makes it very difficult to provide standard solutions that accommodate everyone. This is also the case for restorative dentistry using implants as will be discussed further herein.

The use of implants is a very specific branch of dentistry which has evolved rapidly within the last half century.

An implant is placed in the bone of the jaw where it is secured as the bone grows into very close apposition to the implant. This process is also known as osseointegration. In particular titanium has shown to have very good osseointegration properties and is currently the most preferred material to use for implants.

When osseointegration is complete and the implant is secure in the bone it may subsequently be used as a base for dental restorations and prosthetics. Typically so-called abutments are placed in the implant. The abutment serves as an interface between the implant and the final anatomical restoration, for example a crown or a bridge.

However, in some cases there are constraints on where an implant can be placed, this can for example be due to weak bone tissue or other considerations. Thus, depending on the anatomy of the patient the implant is often placed in different positions, for example at different angles. The abutment has to be designed to correct such difference in placement and angulation. There exists standard angulated abutments, however, these are only useable if the implant are placed within a specific angled interval.

Thus, in order to provide a higher flexibility for placing the implant different customisable abutments have been developed.

In general these can be categorised into two categories.

The first category relates to so-called one-piece customisable abutments, which is illustrated in FIG. 1a.

FIG. 1a shows a dental prosthesis 101 comprising an implant 102, a one-piece customised abutment 103 and a restoration 104, e.g. in the form of a crown.

The implant 102 is placed in the bone tissue 105 of the jaw in an angled position along an implant axis A-A. In general, when referring to the angled position of the implant herein, it should be understood as being in relation to the general anatomy of the restoration and how the restoration protrudes from the jaw.

The one-piece customised abutment extends from the implant along an abutment emergence profile 110. The emergence profile is the shape of the one-piece customised abutment as it relates to the surrounding tissue, typically bone and gingiva, as it extends from the implant towards the exposed gingiva surface 111. The abutment typically ends sub-gingival, i.e. below the exposed gingiva surface, where it extends into the restoration 104. From the abutment the restoration extends along a restoration emergence profile 112 to the exposed gingiva surface from where it extends with an anatomic shape designed to be aesthetic and functional.

Unless explicitly stated otherwise the term "emergence profile" as used herein refers to the emergence profile of the abutment.

The one-piece customised abutment 103 is held in place by an implant screw 106, which is placed in a through-going bore 107 of the customised abutment 103 and engages with threads 108 in the implant to hold the screw and thereby the abutment in place.

The restoration 104 in the form of a crown is placed on the abutment. The crown is designed to fit between two neighbouring teeth 109. Typically the restoration and the abutment are cemented together.

As can be seen the abutment functions as an interface which can be designed so that the restoration can be designed to resemble a tooth as much as possible without being completely restricted to the angle of the placed implant.

The one-piece customised abutment 103 shown in FIG. 1a thus allow the dentist to place the implant much more freely than done before. However, since it is a monolithic one-piece abutment it can only be made of one material.

Typically the one-piece abutment is made of a metal, most commonly the same metal as the implant as this provides a robust and solid base for the restoration 104. However, since the restoration in many cases is made to resemble a tooth the restoration will typically be semi-transparent. This causes the metal of the abutment to shine through creating a greyish look of the final prosthesis which is not esthetical desirable.

Attempts have been made to form the one-piece customisable abutment of a material which has better aesthetic characteristics, such as zirconia. However, this has caused an increase in cases where the abutment breaks, in particular around the connection to the implant.

The other category is the two-piece semi-customisable abutments 203 as shown in FIG. 1 b, which solves some the problems related to the one-piece customisable abutments.

The two-piece abutment 203 is formed of an abutment base 220 and an abutment top 221. The abutment base 220 is provided as a standard unit which fits the specific implant 202. The abutment top 221 is customised and then attached, e.g. by cementing, to the abutment base.

The two-piece abutment 203 allows for the use of two materials. Thus, the abutment base 220 can be formed of a metal, e.g. titanium, and the abutment top 221 can be formed of e.g. zirconia. Thus, the abutment provides a base which is suitable for a dental restoration, such as a crown 204, having a high esthetical quality without risking that the abutment breaks.

However, the use of a standard abutment base 220 results in limitation to the customisation of the abutment top 221. For example in the circled critical area 230 the minimal thickness of the abutment top is compromised due to design restrictions applied by the standard shape of the abutment base.

Moreover, the emergence profile of the abutment, which is defined by the base emergence profile 222 of the abutment base and the top emergence profile 223 of the abutment top, is not fully customisable since the designer is not free to design the base emergence profile 222.

Accordingly, there exists a need to provide an abutment which gives the dentist and the dental laboratory a high degree of freedom of design while at the same time providing a dental prosthesis having high aesthetic and durable characteristics.

SUMMARY

In a first aspect the invention relates to a dental prosthesis comprising an implant, a customised abutment, a restoration and an implant screw for securing the customised abutment to the implant, wherein the implant comprises a screw bore extending from a first end of the implant for receiving at last a part of the implant screw, the customised abutment comprises a through-going bore for receiving at least a part of the implant screw, the screw bore and the through-going bore are coaxially aligned along an implant axis when the implant screw is arranged in the screw bore and the through-going bore, the customised abutment comprises a customised abutment base and a customised abutment top where the customised abutment base and the customised abutment top extends along an abutment axis, and where the implant axis is different from the abutment axis.

This provides a dental prosthesis which is both esthetical and durable, as the choice of e.g. material and design can be chosen individually for the abutment base and the abutment top.

Moreover, the designer also has a high degree of freedom when designing the dental prosthesis since the designer is not limited to a design where the implant axis and the assembly axis are co-axially fixed.

In one embodiment the abutment axis forms an assembly axis along which the customised abutment top and the customised abutment base were assembled during manufacturing.

To ensure proper fit and reduce the risk of misalignment the abutment base and the abutment top are in one embodiment provided with respective base and top guiding means for guiding the abutment base and top together along the abutment axis.

To ensure durability and strength the abutment base is in one embodiment formed of a metal.

In an even further embodiment the abutment base is formed of the same material as the implant, e.g. titanium.

In order to provide an improved esthetical look of the dental prosthesis the abutment top is in one embodiment formed of a material identical to or which has similar esthetical properties as the restoration. The material can for example be a ceramic, lithium-silicate, composites, glass-ceramics or porcelain material. One preferred example is zirconia.

In another aspect the invention relates to a customised two-piece abutment comprising a customised abutment base and a customised abutment top, wherein a through-going bore is formed in at least the abutment base for receiving an implant screw, said through-going bore defines an implant axis, and where the abutment base and the abutment top extends along an abutment axis, where the implant axis is different from the abutment axis.

This provides a two-piece customised abutment which is particular suitable for use in a dental prosthesis which is desired to be both esthetical and durable.

Moreover, the designer also has a high degree of freedom when designing a dental prosthesis comprising such a two-piece abutment.

In one embodiment the abutment axis forms an assembly axis along which the customised abutment top and the customised abutment base were assembled during manufacturing.

As can be understood, the customised abutment described in respect of the current aspect can also comprise the features and embodiments of the customised abutment as described in the previous aspect relating to the dental prosthesis.

In yet another aspect the invention relates to a method for designing a virtual model of a customised abutment for use in designing a virtual dental prosthetic comprising the customised abutment, an implant and a restoration, the method comprising the steps of, obtaining a digital data set representing a dental situation of a patient comprising information on implant type, position and orientation along an implant axis, designing a customised abutment by designing an implant surface for contact to the implant along the implant axis and a restoration surface for contact to a restoration, where an emergence profile of the abutment is designed which separate the implant surface and the restoration surface, splitting the customised abutment into a customised abutment base, which is suited to be arranged adjacent to the implant, and a customised abutment top adjacent to the abutment base, where the customised abutment base and the customised abutment top extends along an abutment axis.

This advantageously allows a designer to design a two-piece customised abutment specifically for an individually placed implant. This is partly possible because the abutment base and the abutment top are customised as defined by the designed emergence profile.

Moreover, a dental prosthesis which is both esthetical and durable may be provided by manufacturing the dental prosthesis having an abutment designed according to the method.

In one embodiment the abutment axis forms an assembly axis along which the customised abutment top and the customised abutment base are adapted to be assembled during manufacturing.

Furthermore, in an additional or alternate embodiment, to ensure proper fit and reduce the risk of misalignment the method further comprises designing respective base and top guiding means on the customised abutment base and the customised abutment top for guiding the customised abutment base and customised abutment top together along the abutment axis.

In one embodiment the method further comprises setting the assembly axis different from the implant axis.

This advantageously gives the designer a high degree of freedom when designing the abutment since the designer is not limited to a design where the implant axis and the assembly axis are co-axially fixed.

In one embodiment the abutment is advantageously split across the emergence profile. This ensures that the split between the customised abutment top and customised abutment base is visibly hidden beneath the gingiva when the physical abutment is placed in the implant.

In one embodiment the method comprises designing an anatomical model of the dental restoration. Based on this the customised abutment is subsequently designed. In this way the abutment is designed partly based on the dental restoration which further ensures a very good fit and final result.

In another aspect the description discloses a user interface comprising a 3D virtual design environment for virtually displaying a virtual abutment defined by a emergence profile extending between an implant surface and a restoration surface, and at least one virtual tool button for modifying the virtual abutment when activated, wherein the at least one virtual tool splits the customised abutment into a customised abutment base and a customised abutment top along a split indication defined by the user.

Such a split indication can for example be a virtual plane provided in the design environment which intersects the virtual abutment where the user wants the split to be placed.

In another embodiment the split indication may for example be provided by a virtual spline drawn by the user on the abutment. The abutment is then split along this spline.

Standard connection means and/or guiding means may be provided between the customised abutment base and the customised abutment top. Such connections or guiding means may be manually designed or provided from template shapes after the split has been provided.

Definitions

The term "dental prosthesis" as used herein refers to the complete artificial tooth or dental replacement placed in the patient. Thus, this term covers the implant, the abutment and the restoration.

The term "dental replacement" as used herein refers to the parts which the lab or the appropriate designer/technician designs. Thus, this term covers the abutment and the restoration.

As will be understood herein when referring to the different parts of the dental prosthesis in relation to the design method as disclosed, it is not a physical part as such, but a virtual representation of a physical part which is described. However, with respect to the final product this will comprise physical parts which have been provided by manufacturing the specific parts based on the virtual representation established during the design process.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

In order to facilitate reading the reference numbers of the drawings are numbered in order to show similar parts for different embodiment. Accordingly, the hundreds digit, i.e. the third digit left of the decimal point indicates the embodiment. The units digits and the tens digit, i.e. the first and second digit left of the decimal point indicates the feature. Thus, for similar features the units and tens digits are similar for separate embodiments, but the hundreds digit will be different.

DETAILED DESCRIPTION

In the following description, reference is made to the accompanying figures, which show by way of illustration how the invention may be practiced.

Figure 1A:
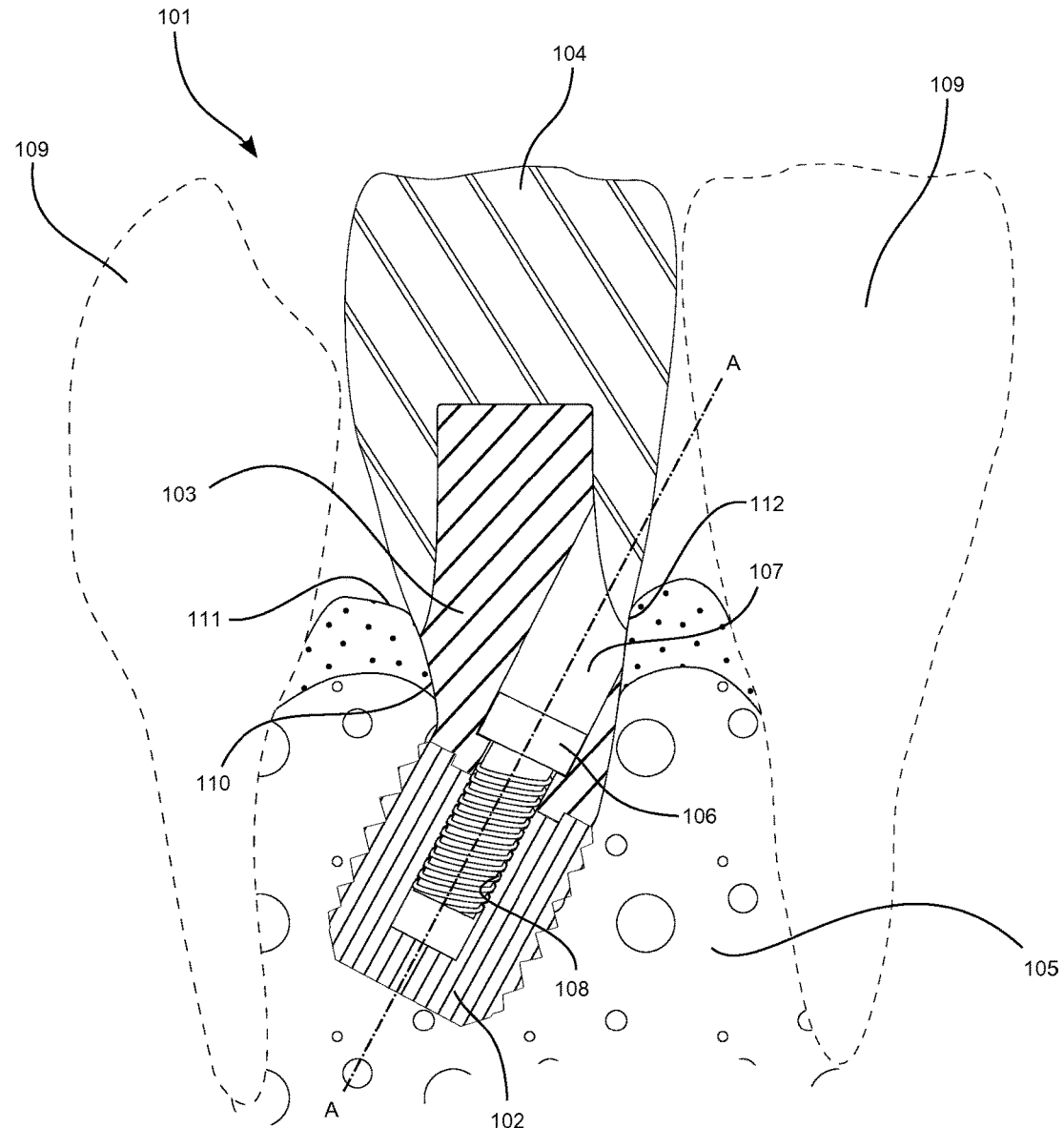
FIG. 1a shows one type of a dental prosthesis according to prior art.
Figure 1B:
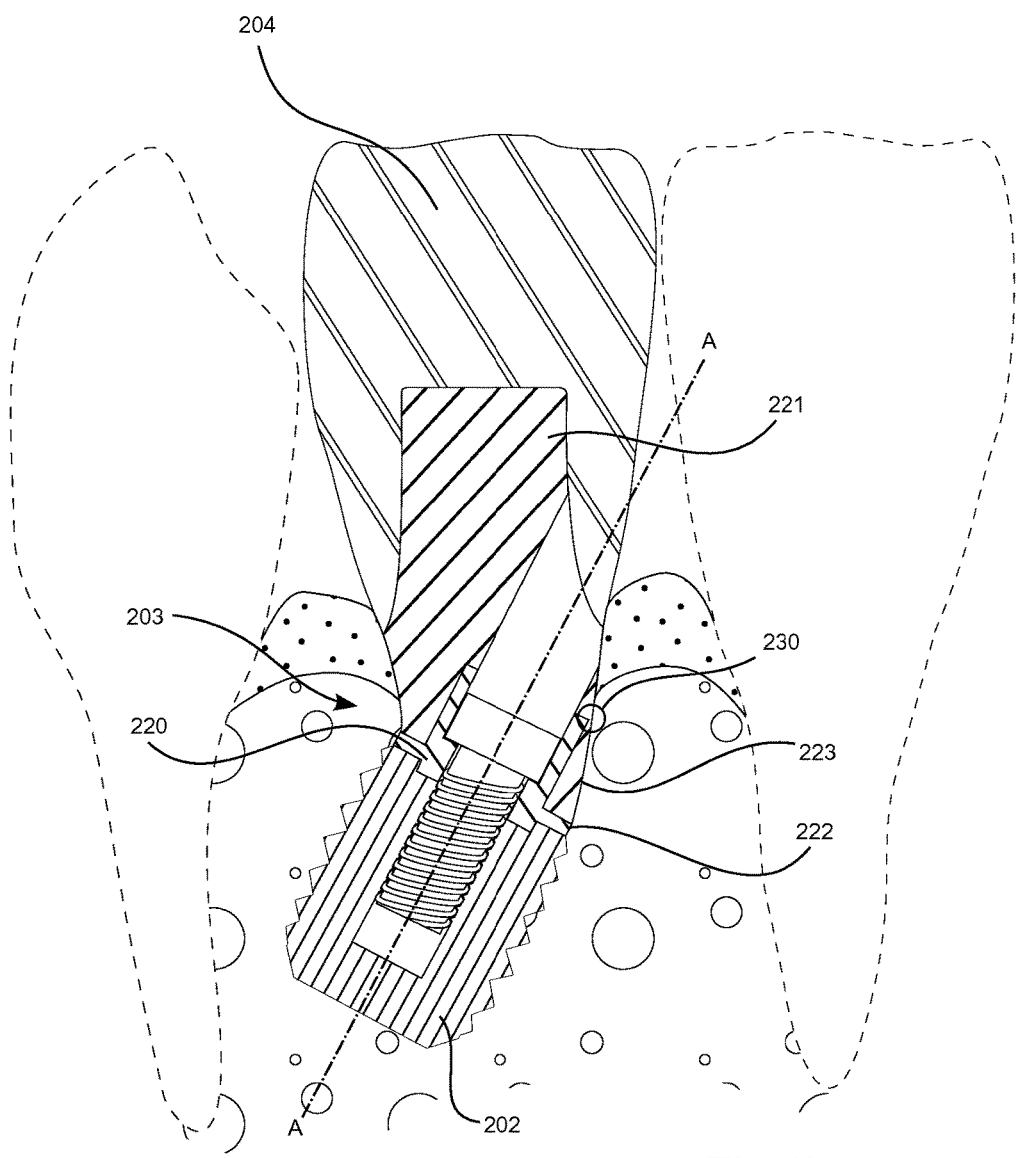
FIG. 1b shows another type of a dental prosthesis according to prior art.
Figure 2:
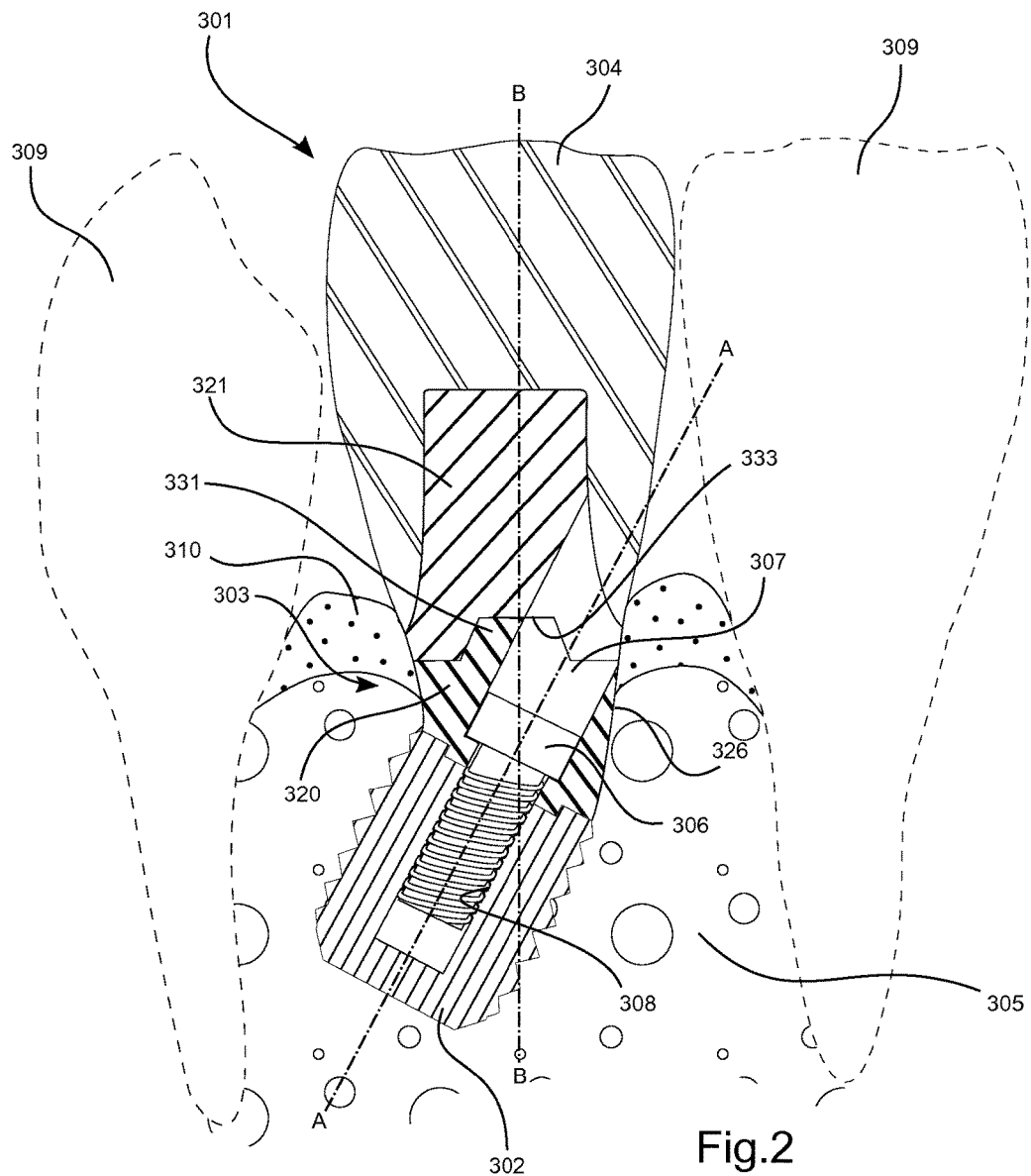
FIG. 2 shows a dental prosthesis according to the invention.

FIG. 2 shows a dental prosthesis 301. The dental prosthesis is formed of an implant 302, a customised abutment 303 and a restoration 304 in the shape of a crown.

The implant 302 is arranged in the bone tissue 305 of the jaw and extends along an implant axis A-A. It should be noted that the drawings are not exact and illustrative only. The implant shown has a one-to-one length to width relationship. Typically this relationship will be two-to-one, however, any other relationship and dimension could be provided within the scope of the present invention.

The abutment 303 is formed of an abutment base 320 and an abutment top 321 which are attached to each other. A through going bore 307 extends through the abutment and is adapted for receiving an implant screw 306 which engages with corresponding internal threads 308 arranged in the implant. The abutment and the implant are arranged in such a way that the through going bore 307 and the implant 302 are co-axially arranged along the implant axis A-A.

The abutment base 320 and the abutment top 321 are attached together, e.g. by cementing, and have been designed such that they are assembled together along an assembly axis B-B. Alternatively, in another embodiment the abutment base and the abutment top may be attached together by a screw connection which extends along the abutment axis B-B.

As can be seen, the implant axis A-A and the assembly axis B-B differs, i.e. they are not co-axial and as shown in the figure are rotated at an angle. Accordingly the abutment base of the abutment is brought into contact with the implant when inserted along the implant axis A-A, and the abutment top of the abutment is brought into contact with the restoration when the restoration is put on along the assembly/abutment axis B-B.

By separating these axes from each other a high degree of design freedom is achieved when designing the abutment. This result in that the dentist can provide a treatment where the patient receives a dental prosthesis which is very aesthetic and durable while at the same time allowing the dentist a high degree of freedom when placing the implant. In particular it provides the freedom to design a dental prosthesis 301, where the abutment 303 has an emergence profile 326 that fits well to the surrounding tissue, e.g. the gingiva 310.

Moreover, the high degree of designer freedom also facilitates the design of the anatomy of the dental restoration, such as the crown 304, so that it fits well to the abutment 303, between neighbouring teeth 309 and have good functionality, e.g. chewing properties and aesthetics.

In order to ensure that the abutment base 320 and the abutment top 321 are aligned correctly during assembly guiding means are provided. In the present embodiment the guiding means are provided in the form of a tapering protrusion 331 on the top facing surface of the abutment base and a tapering recess 333 on the base facing surface of the abutment top. The tapering protrusion 331 and the tapering recess 333 are formed so as to match each other. The tapering walls of the protrusion and recess facilitate the guiding function.

The shape of the tapering protrusion 331 and the tapering recess 333, when seen along the abutment axis B-B, may be formed to ensure proper orientation of the abutment base and abutment top in respect to each other. The shape can thus be irregular, an oval, an asymmetric triangle or any other shape which only matches when aligned in specific desired positions. A notch and groove configuration may also be provided so that the part may only fit together in one unique relative rotational position.

Similar means may be provided between the abutment top and restoration in order to ensure correct fit and orientation. Moreover, the restoration may be attached to the abutment top by cementing or by a separate screw fixation.

Figure 3:
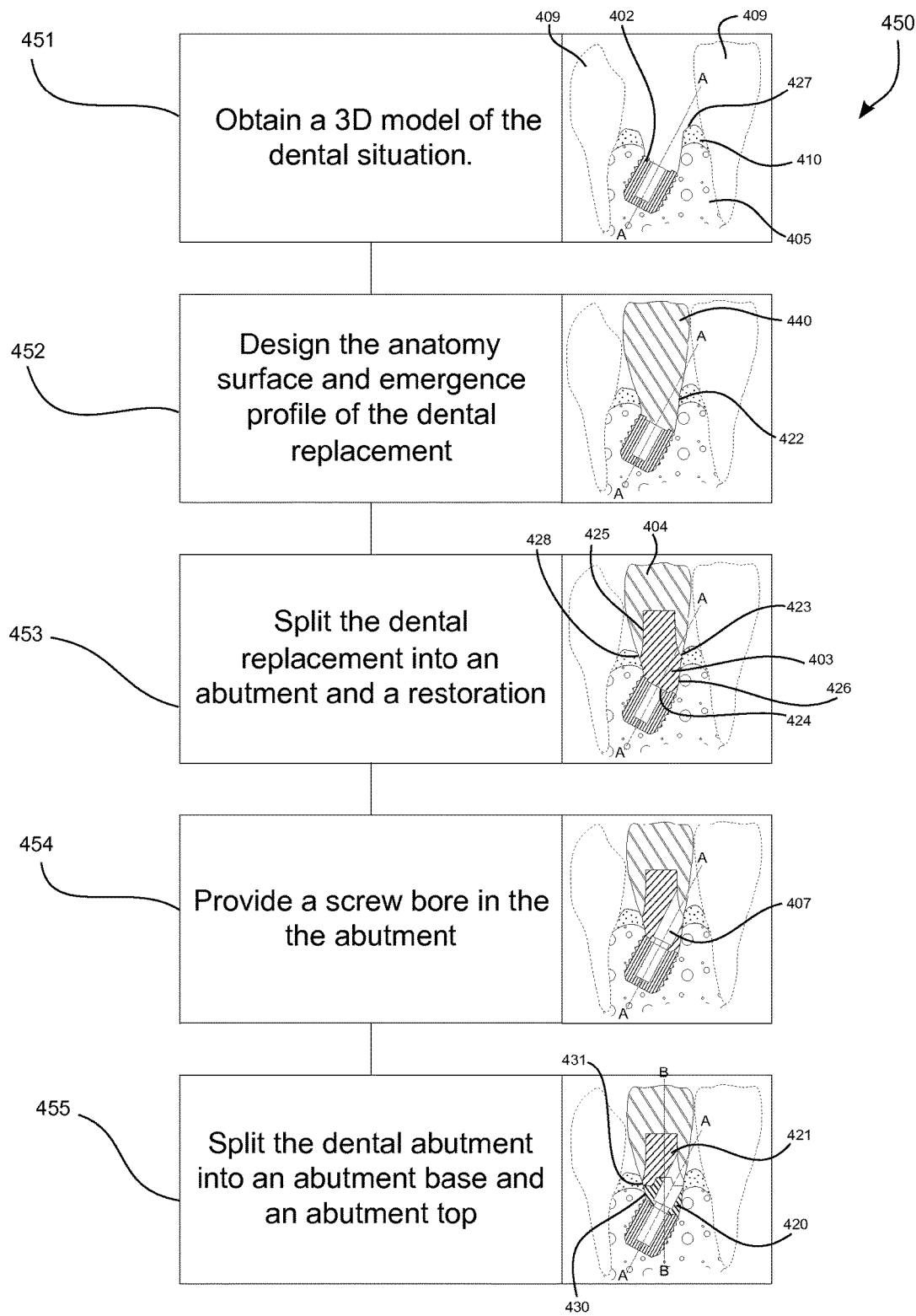
FIG. 3 shows a work flow of how to design a virtual model of a dental prosthesis.

The abutment top maybe provided with different designs. The conical shape shown in FIG. 3 is well known and reliable. However, other designs may also be provided, for example it may have an anatomical surface. An anatomical surface corresponds to the surface of the restoration, although it is offset from the restoration surface. This is for example advantageous in that the designed restoration is provided with an uniform material thickness.

A workflow 450 showing one embodiment of how to design a dental prosthesis having a two-piece customisable abutment as disclosed herein is shown in FIG. 3. The design is preferably performed in a virtual design environment, such as a CAD (Computer Aided Design) program. It should be understood that when referring to different parts in the workflow it is not the physical parts itself that is provided, but virtual models of the respective parts thereof.

In the first step 451, a 3D model of the dental situation is obtained. The 3D model is typically obtained either by scanning a gypsum mould of the dental situation, scanning a dental impression of the dental situation or directly scanning in the oral cavity by using an intra-oral scanner.

The 3D model also includes information on the position of the implant from which an implant axis A-A can be derived. Such information can for example be provided by using so-called scan-abutments during scanning. Briefly discussed the scan-abutment is placed in the implant or the model of the implant in e.g. a gypsum model. When the scan is performed the scan-abutment can then be used to derive the position and angle of the implant. In general this is a well-known method for the person skilled in the art on how to include such information in the scan.

The 3D model can furthermore include information relating to neighbouring teeth 409, gingiva 410, bone tissue 405 and/or additional information on the implant 402, e.g. type and/or size.

In the second step 452 the anatomy of the dental replacement 440 is designed. When designing the anatomy both esthetical and functional characteristics are taken into consideration. In addition the emergence profile 422 of the dental replacement is designed. The emergence profile 422 is the design of the dental replacement at the implant and how its contour follows the gingiva 410 and other surrounding tissue such as the bone tissue 405. The emergence profile 422 of the dental replacement extends from the implant 402 to the expose surface 427 of the gingiva, i.e. the surface of the gingiva which will be free when the dental prosthesis have been finalised, manufactured and placed in the patient.

A well designed emergence profile provides a final dental prosthesis that has a good fit, i.e. not too wide which can result in friction and pain for the patient as the dental prosthesis will press on the surrounding tissue, but not too narrow so that gaps and openings occurs between the dental prosthesis and the surrounding anatomy.

In the third step 453 the dental replacement is split into a restoration 404, in this case a crown, and an abutment 403. The split is preferably placed so that the surface split line 423 is below the upper surface of the gingiva. This divides the emergence profile 422 of the dental replacement into a restoration emergence profile 428 and an abutment emergence profile 426 and hides the surface split line visibly when the dental prosthesis has been placed in the patient.

This creates a virtual model of the abutment 403 which is defined by an implant surface 424 facing the implant and a restoration surface 425 facing the restoration, which are separated by the emergence profile 426 of the abutment.

In the fourth step 454 a screw bore 407 is provided in the abutment. The screw bore is arranged co-axially with the implant axis and is designed to fit an implant screw (not shown) that is able to engage with the specific implant 402 so that the abutment 403 is held in place.

Finally, in the fifth step 455, the abutment is split across the emergence profile 426 into an abutment base 420 having a base emergence profile 430 and an abutment top 421 having a top emergence profile. By allowing the designer to freely apply this split, i.e. so that the assembly direction of the resulting abutment base and abutment top can be provided along an assembly axis B-B different from the implant axis A-A it is possible to place the abutting surfaces of the abutment base and abutment top as desired. This is advantageous in providing the optimal design, both in respect to aesthetic but also durability of the dental prosthesis, since the designer can place the split based on specific design requirements, e.g. material thickness, visibility etc.

Materials for the respective parts can now be chosen. In some embodiments materials are chosen before designing the specific parts, or during the design steps. This allows the design software and designer to take material relevant aspects into consideration when designing. This could for example be minimum/maximum thicknesses for which material failure is avoided, e.g. in respect to breakage, curing etc. Other issues, such as manufacturing limitations may also be taken into consideration.

It should of course be understood that the invention is not limited only to the steps and sequence of steps as discussed in the workflow 450 described above. For example, the abutment could be designed before the anatomy of the dental replacement is designed. Or the step of designing the crown could be left out and designed manually after the customised abutment has been placed in the implant.

The final design may now be sent to manufacturing using manufacturing methods well known to the person skilled in the art such as milling, stereo-lithography or 3D-printing.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

REFERENCE NUMBERS 101. dental prosthesis
102. implant
103. one-piece customised abutment
104. restoration
105. bone tissue
106. implant screw
107. through-going bore 108. threads
109. neighbouring tooth
202. implant
203. two-piece semi customisable abutments
204. restoration
220. abutment base
221. abutment top
230. critical area
301. dental prosthesis
303. customised abutment
304. restoration
305. bone tissue
306. implant screw
307. through going bore
308. threads
309. neighbouring tooth
310. gingiva
320. abutment base
321. abutment top
326. abutment emergence profile
331. tapering protrusion
333. tapering recess
402. implant
403. abutment
404. restoration
405. bone tissue
407. screw bore
409. neighbouring tooth
410. gingiva
420. abutment base
421. abutment top
422. emergence profile
423. surface split line
424. implant surface
425. restoration surface
426. abutment emergence profile
440. dental replacement
450. workflow
451. first step
452. second step
453. third step
454. fourth step
455. fifth step

The invention claimed is:

1. A method for designing a virtual model of a customized abutment using a computer having non-transitory readable medium having instructions which cause the computer to design a virtual model of a customized abutment for use in designing a virtual dental prosthetic comprising the customized abutment, an implant and a restoration, the method comprising:

obtaining a digital data set comprising patient information on a type, position and orientation of an implant along a longitudinal implant axis, virtually designing a customized abutment including an implant surface for contact with the implant along the implant axis and a restoration surface for contact with a restoration, where the implant surface is separate and spaced from the restoration surface, virtually splitting the customized abutment into a customized abutment across an emergence profile base, which is suited to be arranged adjacent to the implant, and a customized abutment top adjacent the customized abutment base, where the customized abutment base and the customized abutment top extend along a longitudinal abutment axis, wherein the customized abutment base and the customized abutment top are separate pieces, wherein the method further comprises setting the abutment axis different from the implant axis.

2. The method according to claim 1, wherein the abutment axis forms an assembly axis along which the customized abutment top and the customized abutment base are adapted to be assembled during manufacturing.

3. The method according to claim 2, wherein the method further comprises setting the abutment axis different from the implant axis.

4. The method according to claim 2, wherein the abutment axis extends along an entire length of the abutment, and the method further comprises setting the abutment axis different from the implant axis.

5. The method according to claim 4, wherein the customized abutment top includes the restoration surface.

6. The method according to claim 1, wherein the method further comprises designing respective base and top guiding means on the customized abutment base and the customized abutment top for guiding the customized abutment base and customized abutment top together along the abutment axis.

7. The method according to claim 1, wherein the method further comprises setting the abutment axis different from the implant axis.

8. The method according to claim 1, where the abutment is designed based on an anatomical design of the dental restoration.

9. The method according to claim 1, wherein the abutment is split across the emergence profile.

10. The method according to claim 1, wherein the customized abutment top includes the restoration surface.

11. The method according to claim 1, wherein the customized abutment top includes the restoration surface.

12. The method according to claim 1, wherein the method comprises obtaining the digital data set with an oral scanner.

* * * * *